(12) United States Patent
Niemann et al.

(10) Patent No.: US 11,555,760 B2
(45) Date of Patent: Jan. 17, 2023

(54) METHOD AND DEVICE FOR DETERMINING TIRE PARTICULATE EMISSIONS IN THE DRIVING OPERATION OF A VEHICLE

(71) Applicant: HELLA GmbH & Co. KGaA, Lippstadt (DE)

(72) Inventors: Thomas Niemann, Delmenhorst (DE); Bastian Kanning, Bremen (DE)

(73) Assignee: HELLA GMBH & CO. KGAA, Lippstadt (DE)

( * ) Notice: Subject to any disclaimer, the term of this patent is extended or adjusted under 35 U.S.C. 154(b) by 210 days.

(21) Appl. No.: 17/006,010

(22) Filed: Aug. 28, 2020

(65) Prior Publication Data

US 2021/0063281 A1 Mar. 4, 2021

(30) Foreign Application Priority Data

Aug. 29, 2019 (DE) .......................... 102019123152.3

(51) Int. Cl.
| | | |
|---|---|---|
| *G01M 17/02* | (2006.01) | |
| *B60H 3/06* | (2006.01) | |
| *G01N 33/00* | (2006.01) | |

(52) U.S. Cl.
CPC .......... *G01M 17/02* (2013.01); *B60H 3/0625* (2013.01); *G01N 33/0031* (2013.01); *G01N 33/0073* (2013.01)

(58) Field of Classification Search
CPC . G01M 17/02; B60H 3/0625; B60H 1/00764; B60H 1/008; B60H 3/0658;

(Continued)

(56) References Cited

U.S. PATENT DOCUMENTS

2016/0280160 A1* 9/2016 MacNeille ......... B60H 1/00771

FOREIGN PATENT DOCUMENTS

| DE | 202006019335 U1 | 6/2008 |
|---|---|---|
| DE | 102008014401 A1 | 10/2008 |

(Continued)

OTHER PUBLICATIONS

Kole PJ, Löhr AJ, Van Belleghem FGAJ, Ragas AMJ. Wear and Tear of Tyres: A Stealthy Source of Microplastics in the Environment. International Journal of Environmental Research and Public Health. 2017; 14(10):1265. https://doi.org/10.3390/ijerph14101265 (Year: 2017).*

*Primary Examiner* — Eric S. McCall
*Assistant Examiner* — Timothy P Graves
(74) *Attorney, Agent, or Firm* — Muncy, Geissler, Olds & Lowe, P.C.

(57) ABSTRACT

The invention relates to a method and a device for determining particulate emissions in the driving operation of a vehicle, in particular of a motor vehicle. According to the invention, provision is made that the device has a sensor system and a control unit and that in driving operation the sensor system and the control unit jointly undertake the function of particulate matter sensors. Here, the sensor system senses driving operation values on the vehicle. From the sensed driving operation values and by means of correlations of driving operation values with particulate matter values determined and stored in advance in the control unit, the control unit estimates the particulate emissions from tyre abrasion of the vehicle. Finally, the invention relates to a vehicle with the device according to the invention.

19 Claims, 1 Drawing Sheet

(58) Field of Classification Search
CPC ....... B60H 2003/0683; G01N 33/0031; G01N 33/0073; B60W 40/12; B60W 50/00; B60W 2420/00; B60W 2422/00; B60R 16/02; G07C 5/08; B60C 11/246; B60C 11/24; B60C 11/243; B60C 23/00
See application file for complete search history.

(56) References Cited

FOREIGN PATENT DOCUMENTS

| | | | |
|---|---|---|---|
| DE | 102014214626 A1 | | 1/2016 |
| DE | 102016108030 A1 | | 12/2016 |
| DE | 102016215900 A1 | * | 3/2018 |
| DE | 102017008745 A1 | | 3/2018 |

* cited by examiner

METHOD AND DEVICE FOR DETERMINING TIRE PARTICULATE EMISSIONS IN THE DRIVING OPERATION OF A VEHICLE

BACKGROUND OF THE INVENTION

Field of the Invention

The invention relates to a method for determining particulate emissions in the driving operation of a vehicle, in particular of a motor vehicle. The invention further relates to a device for determining particulate emissions from tire abrasion in the driving operation of a vehicle. The invention further relates to a vehicle with the device.

Description of the Related Art

In the ambient air of a vehicle, in particular a motor vehicle, which is moving in road traffic, particulate matter is generally present which, depending on concentration and particle size, is harmful to health to varying extent, when this particulate matter arrives into the interior of the vehicle and, for example, is inhaled by a driver of the vehicle. Air from the environment of the vehicle, which is drawn into the interior of the vehicle is therefore generally purified by a particulate matter filter, as is described for example in DE 20 2006 019 335 U1. It is often also desirable to know particulate matter concentrations in the air in the environment of the vehicle and in the air in the interior of the vehicle, in order to be able to decide whether air from the environment is to be blown into the interior of the vehicle, or whether a ventilation of the vehicle interior is to be operated in air recirculation mode. For this, it is known for provide particulate matter sensors, which detect particulate matter in the air. Such an arrangement of particulate matter sensors is known for example from DE 10 2008 014 401 A1. Here, particulate matter with a particle size smaller than 1.0 µm to 0.5 µm, preferably 0.3 µm to 0.5 tm is detected.

It is further known that the vehicle itself can be a source of particulate matter. In particular, exhaust gases of an internal combustion engine provided particulate emissions in the driving operation of a vehicle having the internal combustion engine. From DE 10 2016 108 030 A1 it is known to measure such particulate emissions from exhaust gases by means of a particulate matter sensor.

A further important source of particulate emissions in the driving operation of a vehicle is the tire abrasion on tires of the vehicle. It would therefore be desirable to also know the particulate emissions from tire abrasion which occur in the driving operation of the vehicle. However, a measurement by means of particulate matter sensors would be expensive, in particular as vehicles generally have at least four tires arranged at different locations, wherein a particulate matter sensor would have to be arranged at each tire.

SUMMARY OF THE INVENTION

The invention has therefore set itself as an object to determine in a more favorably-priced manner the particulate emissions from tire abrasion in the driving operation of a vehicle.

The invention solves this problem by a method for determining particulate emissions in the driving operation of a vehicle and by a device for determining particulate emissions from tire abrasion in the driving operation of a vehicle. In a method for determining particulate emissions in the driving operation of a vehicle, in particular a motor vehicle, provision is made according to the invention that a sensor system of the vehicle and a control unit of the vehicle undertake jointly in driving operation the function of particulate matter sensors, wherein the sensor system senses driving operation values on the vehicle and wherein the control unit estimates the particulate emissions from tire abrasion of the vehicle from the sensed driving operation values and by means of correlations, previously determined and stored in the control unit, of driving operation values with particulate matter values.

With a device for determining particulate emissions in the driving operation of a vehicle, in particular a motor vehicle, provision is made according to the invention that the device has the sensor system and the control unit, which are configured and interconnected in such a way in order to jointly undertake the function of particulate matter sensors in driving operation, wherein the sensor system is configured for sensing driving operation values on the vehicle and wherein the control unit is configured for estimating the particulate emissions from e abrasion of the vehicle from the sensed driving operation values and by means of correlations, previously determined and stored in the control unit, of driving operation values with particulate matter values.

The invention solves the problem further with a vehicle, in particular a motor vehicle, having the device according to the invention for estimating particulate emissions in the driving operation of the vehicle.

The invention is based on the finding that particulate emissions on tires of the vehicle vary depending on different operating situations in driving operation. The invention is further based on the finding that these operating situations can be detected from driving operation values of different sensors installed on the vehicle. The invention is further based on the finding that after a learning phase, in which through measurements with particulate matter sensors and simultaneous measurements by means of a sensor system, which in particular has several sensors, in a subsequent driving operation the particulate matter sensors can be dispensed with, by the particulate emissions from tire abrasion being estimated proceeding from the driving operation values which are sensed on the vehicle. A corresponding learning for this needs only to take place once for example in a prototype of the vehicle and can subsequently be used in numerous vehicles of identical construction, in order to estimate the particulate emissions on these vehicles, without having to equip these vehicles with particulate matter sensors for this.

Advantageously, provision is made that the sensor system senses driving operation values for at least one driving operation parameter of tires of the vehicle, and the control unit takes these driving operating values into consideration for estimating the particulate emissions. In particular, the at least one driving operation parameter of the tires comprises one, several or all of the following parameters: tire internal pressure, tire type, tire state, tread depth. The tire internal pressure is preferably determined here for each tire by means respectively of a pressure sensor installed on the respective tire and transmitted for example via radio to the control unit. For the detection of the tire type, the tire state and the tread depth, preferably a sensor is arranged in the environment of the respective tire, in particular in the wheel arch of the wheel having the tire.

Advantageously, the sensor system senses alternatively or additionally driving operation values for at least one driving operation parameter of the roadway on which the vehicle is travelling, wherein the control unit takes these driving operation values into consideration in turn for estimating the particulate emissions. The driving operation parameters of the roadway comprise in particular one, several or all of the following parameters: roadway temperature, roadway texture, intermediate layer. For measuring the roadway temperature, preferably a temperature sensor is provided, for example in the front region of the vehicle. A separate sensor is preferably provided for measuring the roadway texture and the intermediate layer, therefore the type of substratum.

Preferably, provision is further made that the sensor system senses driving operation values for at least one driving operation parameter for the interaction between tires and roadway, in particular the slip parameter. The slip on the respective tire is preferably determined together with the tire type, the tire state and the tread depth by means of the same sensor or with the same sensors.

Advantageously, for estimating the particulate emissions the control unit also takes into consideration one, several or all of the following further, in particular set or measured, operating parameters provided for the control unit, from the driving operation of the vehicle: air temperature, speed of travel, acceleration or deceleration, steering angle. Moreover, further parameters which are not named here can be additionally used by the control unit for estimating the particulate emissions. The correlations of driving operation values with particulate matter values which are stored in the control unit are preferably determined previously by means of measurements on a vehicle which is in particular of identical or similar construction. Here, particulate matter sensors, which are arranged for this in the wheel arches of the vehicle, measure the particulate matter values. In the subsequent driving operation, the particulate matter sensors are then no longer required for carrying out the method.

In an advantageous embodiment of the invention, provision is made that the control unit detects when the estimated particulate emissions exceed an upper threshold, and then by comparing the sensed driving operation values with typical combinations of measurable driving operation values which were determined for several different operating situations and are stored together with these operating situations in the control unit, identifies an operating situation which is responsible for the increased particulate emissions. Thus, increased particulate emissions are detected with the aid of the driving operation values which are determined by means of the sensor system.

In addition, provision is preferably made that the control unit, depending on the respectively identified operating situation, proposes or initiates an operating strategy for the vehicle, likewise derived in advance from the respective operating situation and stored in the control unit, in order to reduce the particulate emissions. The invention can therefore be used to prevent operating situations of the vehicle which lead to increased particulate emissions. An operating strategy is proposed for example in that a corresponding display is presented to the driver of the vehicle in the form of a backlit pictogram or in the form of a plaintext. An automatic running of the operating strategy is also possible, wherein according to a further development the operating strategy Is only initiated automatically when this is not noticeable for the driver of the vehicle.

The operating strategy advantageously contains a driving dynamics. Alternatively or additionally, the operating strategy contains a route selection for the vehicle. According to a further development of the invention, provision is made that in combination with a navigation system for travelled routes particulate emissions are determined and with repeated travelling of the routes therefore if applicable an alternative route selection is proposed, which leads to comparatively lower particulate emissions.

In an additional further development of the invention, provision is made that as a function of the estimated particulate emissions, the control unit actuates a filter system, in particular for air in the region of the wheel arches, in order to extend maintenance intervals of the filter system, in particular change intervals of a filter medium. In particular, provision is made here that the control unit actuates the filter system to filter air only, in particular through filters of the filter system, when the control unit estimates that the particulate emissions rise over an upper threshold. Thereby, the filter medium of the filter system dirties less intensively through microplastics and/or dripping oils and/or heavy metals when the particulate emissions make no filtering necessary, so that the filter system can be used for a longer time without a change of the filter medium.

According to this embodiment, the device according to the invention has a filter system accordingly. The control unit is configured here and interconnected with the filter system in such a way that the control unit actuates the filter system as a function of the estimated particulate emissions, in order to extend maintenance intervals of the filter system, in particular change intervals of a filter medium.

Advantageously, the control unit actuates the filter system to direct air through a bypass past a filter medium when the control unit estimates that the particulate emissions are not rising above the upper threshold. Alternatively, in this case the air throughput without bypass through the filter is interrupted. The device according to the invention advantageously has the switchable bypass, wherein the control unit is configured for the corresponding actuation of the filter system in order to filter the air only on exceeding the threshold and otherwise to direct it if necessary through the bypass past the filter medium.

In an additional further development of the method according to the invention, provision is made that the control unit transmits the estimated particulate matter values, in particular via a radio connection, to a traffic control system. Thereby, the traffic control system can link the particulate matter values, generated at various locations in the road network, in order to control the traffic for example in such a way that at specific locations in the road network the particulate matter values do not exceed a defined threshold.

In addition, in a further development based hereon, provision is made that for area-wide reduction of particulate emissions, the traffic control system transmits an operating strategy to each control unit and/or to a control unit of another vehicle as a function of the transmitted particulate matter values. The vehicle is thereby not only directed by the traffic control system with driving instructions from outside the vehicle, but driving instructions are emitted directly in the vehicle or operating strategies are applied which reduce the individual particulate emissions which originate from this vehicle, or move them to another location in the road network.

The device has optionally further means for carrying out all the method steps according to a possible embodiment of the method according to the invention.

The vehicle, which in particular is a motor vehicle, has in accordance with the invention the device according to the invention for the estimating of particulate emissions in driving operation of the vehicle. Otherwise, the vehicle is constructed in a conventional manner and therefore does not need to be described in further detail.

BRIEF DESCRIPTION OF THE DRAWINGS

Further embodiments will emerge from the claims, from the drawings and from the following description of a preferred example embodiment of the invention, illustrated in the drawings. In the drawings there are shown:

DETAILED DESCRIPTION

Figure 1:
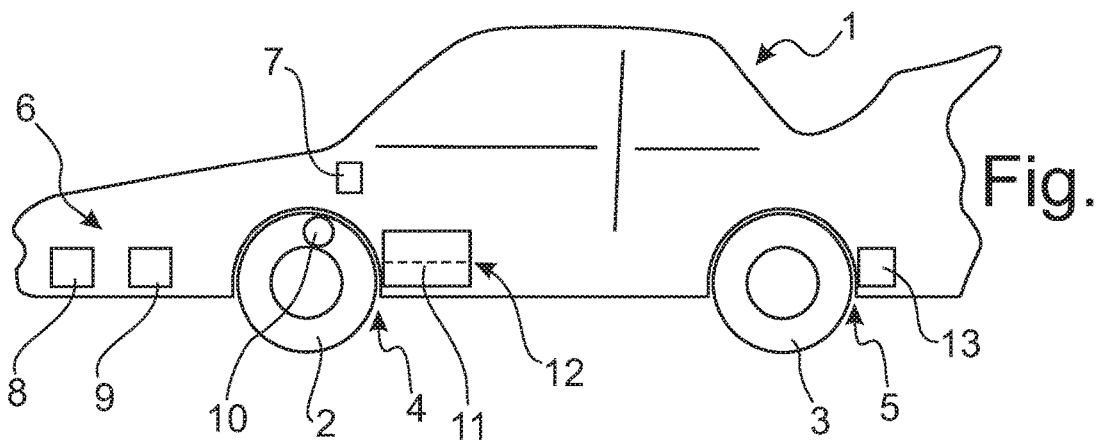
FIG. 1: a vehicle with a device for determining particulate emissions in the driving operation of the vehicle according to a preferred example embodiment of the invention in simplified diagrammatic representation.

FIG. 1 shows a vehicle 1 according to a preferred example embodiment of the invention. The vehicle 1 is, for example, a motor vehicle, in particular a passenger car. However, the invention can also be used in the same manner in utility vehicles such as trucks. The vehicle 1 has four wheels, not designated, with tires, of which the front left tire of the front left wheel is designated by reference number 2, and the rear left tire of the rear left wheel is designated by reference number 3. The front left tire 2 is arranged in a front left wheel arch 4. The rear left wheel with the rear left tire 3 is arranged in a rear left wheel arch 5.

The vehicle 1 is equipped with a sensor system 6 and with a control unit 7, which receives and further processes driving operation values which are sensed by means of the sensor system 6. In particular, the control unit 7 estimates with the driving operation values provided by the sensor system 6 in the driving operation of the vehicle 1 particulate emissions which arise from tire abrasion of the vehicle 1. A particulate matter sensor is not used for this. Only for the learning of the control unit 7 are particulate matter sensors installed, for example in a prototype vehicle additionally to the sensor system 6, in the wheel arches 4 and 5 and alternatively or additionally in the wheel arches, which are not designated, on the right-hand side of the vehicle, in order to be able to detect characteristic driving operation values of individual sensors of the sensor system 6 at which increased particulate matter values occur.

The sensor system 6 comprises a roadway temperature sensor 8 for measuring the roadway temperature, a roadway condition sensor 9 for measuring the roadway texture and the intermediate layer of the roadway, a tire internal pressure sensor 10 for measuring the tire internal pressure in the front left tire 2, and alternatively or additionally tire internal pressure sensors, which are not designated, preferably in the rear left tire 3 and in each further tire of the vehicle 1, a tire condition sensor 11 for sensing the tire type, the tire state and the tread depth of the front left tire 2 and alternatively or additionally a tire condition sensor in the region of the front right tire of the vehicle 1, a slip sensor 12, integrated into the tire condition sensor 11, for sensing the slip between the front left tire 2 and the roadway, and an independent slip sensor 13 for sensing the slip between the rear left tire 3 and the roadway. The sensor system 6 contains alternatively or additionally a roadway condition sensor, tire internal pressure sensors, a tire condition sensor for integrated slip sensor and an independent slip sensor on the right side of the vehicle in an arrangement in accordance with the sensors 10, 11, 12 and 13 on the left side of the vehicle.

The tire condition sensors 11 are arranged only at the front wheel arches 4 of the vehicle 1, but alternatively or additionally in alternative example embodiments of the invention can also be arranged at the rear wheel arches 5 for sensing the tire condition at the rear tires 3. Here, the slip sensor 13 can also be integrated into the tire condition sensor 11. Alternatively to the illustrated example embodiment, the integrated slip sensor 12 can also be arranged independently in accordance with the slip sensor 13 in the front wheel arch 4.

Deviating from the illustrated example embodiment, individual sensors of the sensor system 6 can be omitted. In a further alternative to the illustrated example embodiment, further sensors can also be contained in the sensor system 6 and their signals can be evaluated by the control unit 7.

Figure 2:
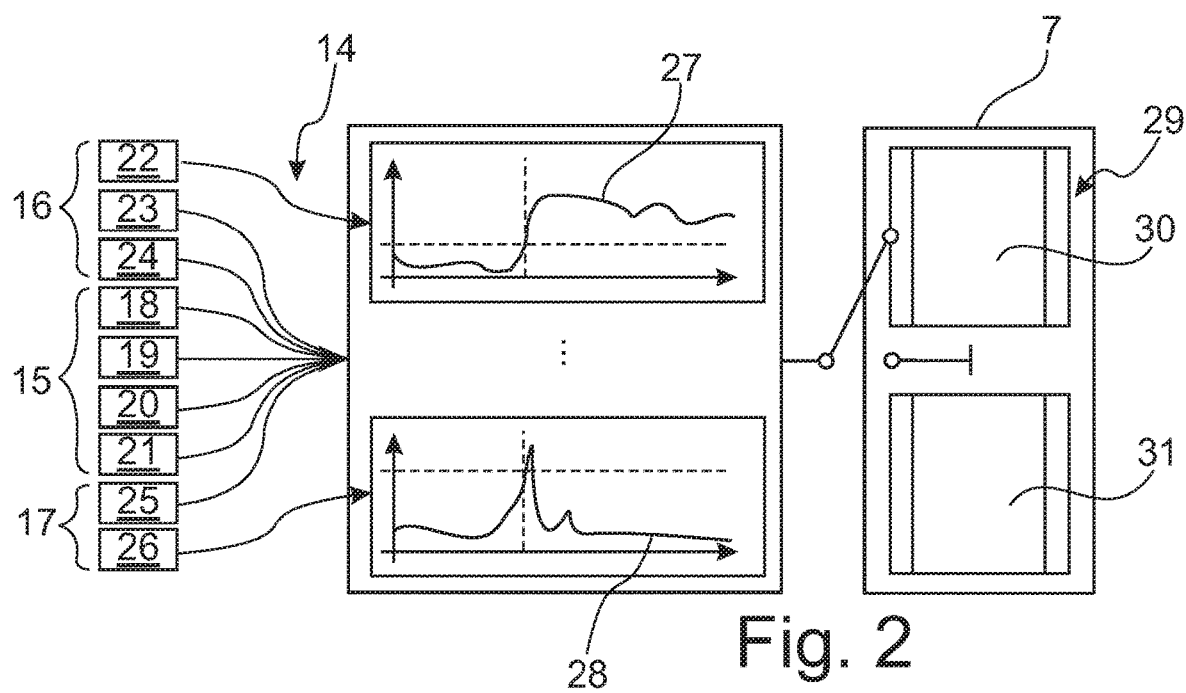
FIG. 2: a diagrammatic representation to illustrate the evaluation, according to the invention, of signals of a sensor system and deriving an operating strategy for the vehicle.

FIG. 2 illustrates an evaluation of driving operation values 14, sensed by means of the sensor system 6, or signals by means of the control unit 7. The driving operation values 14 are detected here for several driving operation parameters, namely for at least one driving operation parameter 15 of tires 2, 3 of the vehicle 1, for at least one driving operation parameter 16 of the roadway and for at least one driving operation parameter 17 for the interaction between the tires 2, 3 and the roadway. The driving operation parameters 15 of the tires 2, 3 of the vehicle 1 are sensed here by means of the tire internal pressure sensors 10 and the tire condition sensors 11, and comprise the tire internal pressure 18, the tire type 19, the tire state 20 and the tread depth 21 of the respective tire 2, 3. The driving operation parameters 16 of the roadway are sensed by means of the roadway temperature sensor 8 and the roadway condition sensor 9 and comprise the roadway temperature 22, the roadway texture 23 and the intermediate layer 24 in the roadway. The driving operation parameters 17 for the interaction between the tires 2, 3 and the roadway contain the slip 25 between the front tire 2 and the roadway and the slip 26 between the rear tire 3 and the roadway.

By way of example, a first signal 27 formed from the driving operating values 14, and a second signal 28 formed from the driving operation values 14 of the slip 26 between the rear tires 3 and the roadway, are illustrated over time in FIG. 2. The control unit 7 evaluates the signals 27 and 28, detects typical characteristics therein, with which particulate emissions can be concluded which lie above a threshold, therefore increased particulate emissions and, after the detection of such a characteristic signal, selects a predefined and stored operating strategy 29, which appears to be suitable to reduce the particulate emissions, estimated by means of the sensor system 6 and the control unit 7, in the region of the wheel arches 4, 5. A specific driving dynamics 30 is such an operating strategy 29. A route selection 31 is an alternative operating strategy 29.

Figure 3:
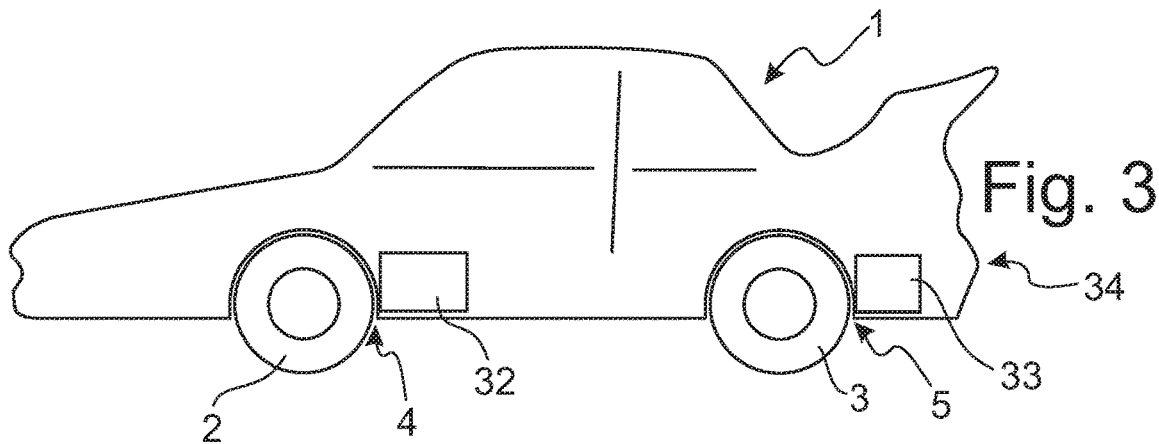
FIG. 3: the vehicle of FIG. 1 with air filters in its wheel arches.

FIG. 3 shows a further development of the vehicle 1 of FIG. 1, which is additionally equipped with air filters in the wheel arches 4, 5. An air filter arranged in the front left wheel arch 4 is designated by reference number 32. An air filter arranged in the rear left wheel arch 5 is designated by reference number 33. The air filters 32 and 33 are part of a filter system 34 of the vehicle 1 which is constructed to filter air at the point of origin of particulate emissions, namely in the region of the wheel arches. Otherwise, the vehicle 1 is equipped in accordance with the illustration in FIG. 1, wherein in particular the sensor system 6 and the control unit 7 are not drawn again, for reasons of clarity.

All the features named in the above description and in the claims are able to be combined in any desired selection with the features of the independent claims. The disclosure of the invention is therefore not limited to the described and/or claimed combinations of features, rather all appropriate combinations of features in the scope of the invention are to be regarded as disclosed.

The invention claimed is:

1. A method for determining particulate emissions in the driving operation of a vehicle,
wherein a sensor system of the vehicle and a control unit of the vehicle in driving operation undertake jointly the function of particulate matter sensors,
wherein the sensor system senses driving operation values on the vehicle,
wherein the control unit estimates, from the sensed driving operation values and by means of correlations of driving operation values with particulate matter values determined and stored in advance in the control unit, the particulate emissions from tire abrasion of the vehicle, and
wherein, depending on the estimated particulate emissions, the control unit actuates a filter system, for at least one of microplastics, dripping oils and heavy metals, in order to extend maintenance intervals of the filter system, in particular change intervals of a filter medium.

2. The method according to claim 1, wherein the sensor system senses driving operation values for at least one driving operation parameter of tires of the vehicle, and the control unit takes these driving operation values into consideration for estimating the particulate emissions.

3. The method according to claim 2, wherein the driving operation parameter of the tires comprises at least one of tire internal pressure, tire type, tire state and, tread depth.

4. The method according claim 1, wherein the sensor system senses driving operation values for at least one driving operating parameter of a roadway on which the vehicle is travelling, and the control unit takes these driving operation values into consideration for estimating the particulate emissions.

5. The method according to claim 4, wherein the driving operation parameter of the roadway comprises at least one of the following parameters:
roadway temperature, roadway texture and intermediate layer.

6. The method according to claim 1, wherein the sensor system senses driving operation values for at least one driving operation parameter for an interaction between tires and roadway, in particular a slip parameter.

7. The method according to claim 1, wherein, for estimating the particulate emissions, the control unit also takes into consideration at least one of the following further operating parameters from the driving operation of the vehicle which are provided, in particular set or measured, for the control unit: air temperature, speed of travel, acceleration or deceleration, steering angle.

8. The method according to claim 1, wherein the correlations, stored in the control unit, of driving operation values with particulate matter values are determined in advance by means of measurements on a vehicle in particular of identical construction, wherein particulate matter sensors which are arranged for this in the wheel arches of the vehicle measure the particulate matter values.

9. The method according to claim 1, wherein the control unit detects when the estimated particulate emissions exceed an upper threshold, and then identifies an operating situation which is responsible for the increased particulate emissions by comparing the sensed driving operation values with typical combinations of measurable driving operation values which were determined in advance for several different operating situations and are stored together with these operating situations in the control unit.

10. The method according to claim 9, wherein, depending on the respectively identified operating situation, the control unit suggests or initiates an operating strategy for the vehicle which is likewise derived in advance from the respective operating situation and stored in the control unit, in order to reduce the particulate emissions.

11. The method according to claim 10, wherein the operating strategy contains a driving dynamics and a route selection for the vehicle.

12. The method according to claim 1, wherein the control unit actuates to only filter air when the control unit estimates that the particulate emissions rise above an upper threshold.

13. The method according to claim 12, wherein the control unit actuates the filter system to direct air through a bypass past a filter medium when the control unit estimates that the particulate emissions do not rise above the upper threshold.

14. The method according to claim 1, wherein the control unit transmits the estimated particulate emissions to a traffic control system, in particular via a radio connection.

15. The method according to claim 14, wherein, for area-wide reduction of particulate emissions, the traffic control system transmits an operating strategy to this control unit and/or to a control unit of another vehicle as a function of the transmitted particulate matter values.

16. A device for determining particulate emissions in the driving operation of a vehicle, the device comprising:
a sensor system;
a control unit; and
a filter system,
wherein the sensor system and the control unit are configured and interconnected in such a way in order to jointly undertake, in driving operation, the function of particulate matter sensors,
wherein the sensor system is configured for sensing driving operation values on the vehicle,
wherein the control unit is configured for estimating the particulate emissions from tire abrasion of the vehicle from the sensed driving operation values and by means of correlations of driving operation values with particulate matter values determined and stored in advance in the control unit, and
wherein the control unit is configured and interconnected with the filter system in such a way that the control unit actuates the filter system as a function of the estimated particulate emissions in order to extend maintenance intervals of the filter system, in particular change intervals of a filter medium.

17. The device according to claim 16, wherein the filter system has a switchable bypass, which is actuated by the control unit, to filter air through a filter medium when the control unit estimates that the particulate emissions exceed an upper threshold, and otherwise to direct the air past the filter medium through the bypass.

18. A vehicle, in particular a motor vehicle, with a device according to claim 16 for estimating particulate emissions from tire abrasion in the driving operation of the vehicle.

19. A device for determining particulate emissions in the driving operation of a vehicle, the device comprising:
a sensor system; a control unit,
wherein the sensor system and control unit are configured and interconnected in such a way in order to jointly undertake, in driving operation, the function of particulate matter sensors,
wherein the sensor system is configured for sensing driving operation values on the vehicle, wherein the control unit is configured for estimating the particulate emissions from tire abrasion of the vehicle from the sensed driving operation values and by means of correlations of driving operation values with particulate matter values determined and stored in advance in the control unit, wherein the sensor system and the control unit in driving operation undertake jointly the function of particulate matter sensors, wherein the sensor system senses driving operation values on the vehicle, wherein the control unit estimates, from the sensed driving operation values and by means of correlations of driving operation values with particulate matter values determined and stored in advance in the control unit, the particulate emissions from tire abrasion of the vehicle, and wherein, depending on the estimated particulate emissions, the control unit actuates a filter system, for at least one of microplastics, dripping oils and heavy metals, in order to extend maintenance intervals of the filter system, in particular change intervals of a filter medium.

\* \* \* \* \*